United States Patent
Park et al.

(10) Patent No.: US 11,307,195 B2
(45) Date of Patent: Apr. 19, 2022

(54) IMPACT BLOOD SPLATTERS GENERATION EXPERIMENTAL APPARATUS CAPABLE OF MEASURING APPLIED FORCE AND METHOD OF GENERATING IMPACT BLOOD SPLATTERS USING THE SAME

(71) Applicant: REPUBLIC OF KOREA(NATIONAL FORENSIC SERVICE DIRECTOR MINISTRY OF PUBLIC ADMINISTRATION AND SECURITY), Wonju-si (KR)

(72) Inventors: Nam Kyu Park, Bucheon-si (KR); Jae Mo Goh, Wonju-si (KR); Jin Pyo Kim, Daejeon (KR); Young Il Seo, Wonju-si (KR); Eun Ah Joo, Yongin-si (KR); Je Hyun Lee, Wonju-si (KR); Sang Yoon Lee, Wonju-si (KR); Dong A Lim, Daejeon (KR); Kyung Mi Kim, Namyangju-si (KR)

(73) Assignee: REPUBLIC OF KOREA(MANAGEMENT: NATIONAL FORENSIC SERVICE DIRECTOR, MINISTRY OF PUBLIC ADMINISTRATION AND SECURITY), Wonju-si (KR)

( * ) Notice: Subject to any disclaimer, the term of this patent is extended or adjusted under 35 U.S.C. 154(b) by 334 days.

(21) Appl. No.: 16/709,502

(22) Filed: Dec. 10, 2019

(65) Prior Publication Data
US 2021/0132038 A1    May 6, 2021

(30) Foreign Application Priority Data
Nov. 6, 2019  (KR) .......................... 10-2019-0141093

(51) Int. Cl.
*G01N 33/49* (2006.01)
*G01N 3/307* (2006.01)

(52) U.S. Cl.
CPC ............. *G01N 33/49* (2013.01); *G01N 3/307* (2013.01)

(58) Field of Classification Search
CPC ........ G01N 33/49; G01N 3/307; G01N 11/00; B01L 99/00; G01D 7/00; G01L 5/0033; G01B 3/56; G06F 17/10
See application file for complete search history.

(56) References Cited

U.S. PATENT DOCUMENTS

| 2011/0201099 A1* | 8/2011 | Anderson ................. G01N 1/10 435/287.2 |
| 2019/0231222 A1* | 8/2019 | Ahmad ................. A61B 5/0836 |

FOREIGN PATENT DOCUMENTS

| KR | 1588323 B1 * | 1/2013 | ............. G01B 21/04 |
| KR | 10-1588323 B1 | 1/2016 | |

\* cited by examiner

Primary Examiner — Francis C Gray
(74) Attorney, Agent, or Firm — Hauptman Ham, LLP

(57) ABSTRACT

An impact blood splatters generation experimental apparatus capable of measuring an applied force includes: a hammer including a rod-shaped body portion, a head portion formed at one end of the body portion, and a striking portion formed on one side of the head portion; a housing receiving a certain amount of blood thereon and including a striking surface on which the striking portion may strike; a tensile force gauge attached to an outer surface of the housing; an elastic member having one end connected to the body portion and the other end connected to the tensile force gauge; and a display unit displaying a force applied to the hammer, the force being measured by the tensile force gauge, when a user lifts the hammer to strike the striking surface.

7 Claims, 6 Drawing Sheets

IMPACT BLOOD SPLATTERS GENERATION EXPERIMENTAL APPARATUS CAPABLE OF MEASURING APPLIED FORCE AND METHOD OF GENERATING IMPACT BLOOD SPLATTERS USING THE SAME

CROSS-REFERENCE TO RELATED APPLICATION

This application claims the benefit of Korean Patent Application No. 10-2019-0141093, filed on Nov. 6, 2019, in the Korean Intellectual Property Office, the disclosure of which is incorporated herein in its entirety by reference.

BACKGROUND

1. Field

One or more embodiments relate to an impact blood splatters generation experimental apparatus capable of measuring an applied force and a method of generating impact blood splatters using the same.

2. Description of the Related Art

Blood is often left in a violent crime scene. A blood morphology analysis is a scientific investigation method that reconstructs the crime scene by analyzing various types of blood such as blood by simple contact or blood splashed from a weapon that strikes the victim. Specific findings from the blood morphology analysis include blood spots of scattered blood, the movement of the victim and the perpetrator at the time of the blood, and the type of weapon used. The blood morphology analysis may find specific findings and solve criminal cases.

In a bleeding case, knowing the point where a strike was made in a blood spot may precisely reconstruct the crime scene and provide important clues in solving criminal cases. Therefore, when impact blood splatters are generated using an apparatus capable of generating impact blood splatters, it is possible to accurately reconstruct the bleeding case by accurately analyzing the shape and the blood spot of the impact blood splatters.

[Prior art document] Korean Patent No. 10-1588323 (registered on Jan. 19, 2016)

SUMMARY

One or more embodiments include an impact blood splatters generation experimental apparatus capable of measuring an applied force, which may study and analyze the shape of impact blood splatters and a blood spot together with the applied force, and a method of generating impact blood splatters using the impact blood splatters generation experimental apparatus.

According to an embodiment, an impact blood splatters generation experimental apparatus capable of measuring an applied force includes: a hammer including a rod-shaped body portion, a head portion formed at one end of the body portion, and a striking portion formed on one side of the head portion; a housing receiving a certain amount of blood thereon and including a striking surface on which the striking portion may strike; a tensile force gauge attached to an outer surface of the housing; an elastic member having one end connected to the body portion and the other end connected to the tensile force gauge; and a display unit displaying a force applied to the hammer, the force being measured by the tensile force gauge, when a user lifts the hammer to strike the striking surface.

The impact blood splatters generation experimental apparatus may further include: a support fixing member including a support portion coupled to the other end of the body portion such that the striking portion strikes the striking surface while the body portion rotates at a constant angle; and a fixing portion for fixing the support portion to the ground.

The impact blood splatters generation experimental apparatus may further include: a blood injection member including a blood storage portion located inside the housing and storing and discharging the blood; and a blood injection portion for injecting a certain amount of blood discharged from the blood storage portion into a certain position of the striking surface.

The impact blood splatters generation experimental apparatus may further include an angle measurer for measuring a rotation angle of the body portion, wherein the display unit may further display an angle measured by the angle measurer.

One or more embodiments include a method of generating impact blood splatters using an impact blood splatters generation experimental apparatus includes: lifting a hammer including a rod-shaped body portion, a head portion formed at one end of the body portion, and a striking portion formed on one side of the head portion; measuring the magnitude of force applied to the hammer by a tensile force gauge connected to the other end of the elastic member having one end connected to the body portion; generating impact blood splatters by striking a striking surface in which a certain amount of blood is received by the striking portion; and observing and analyzing the shape and location of the impact blood splatters according to the magnitude of the force applied to the hammer.

The striking surface may have a constant height from the ground and may be formed on an upper surface of a housing with the tensile force gauge on the outer surface.

The lifting of the hammer, the measuring of the magnitude of the force applied to the hammer, the generating of impact blood splatters, and the observing and analyzing of the shape and location of the impact blood splatters may be performed by rotatably fixing the other end of the body portion so as to rotate the body portion at a certain angle when the hammer is lifted, and by changing a rotation angle of the body portion.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
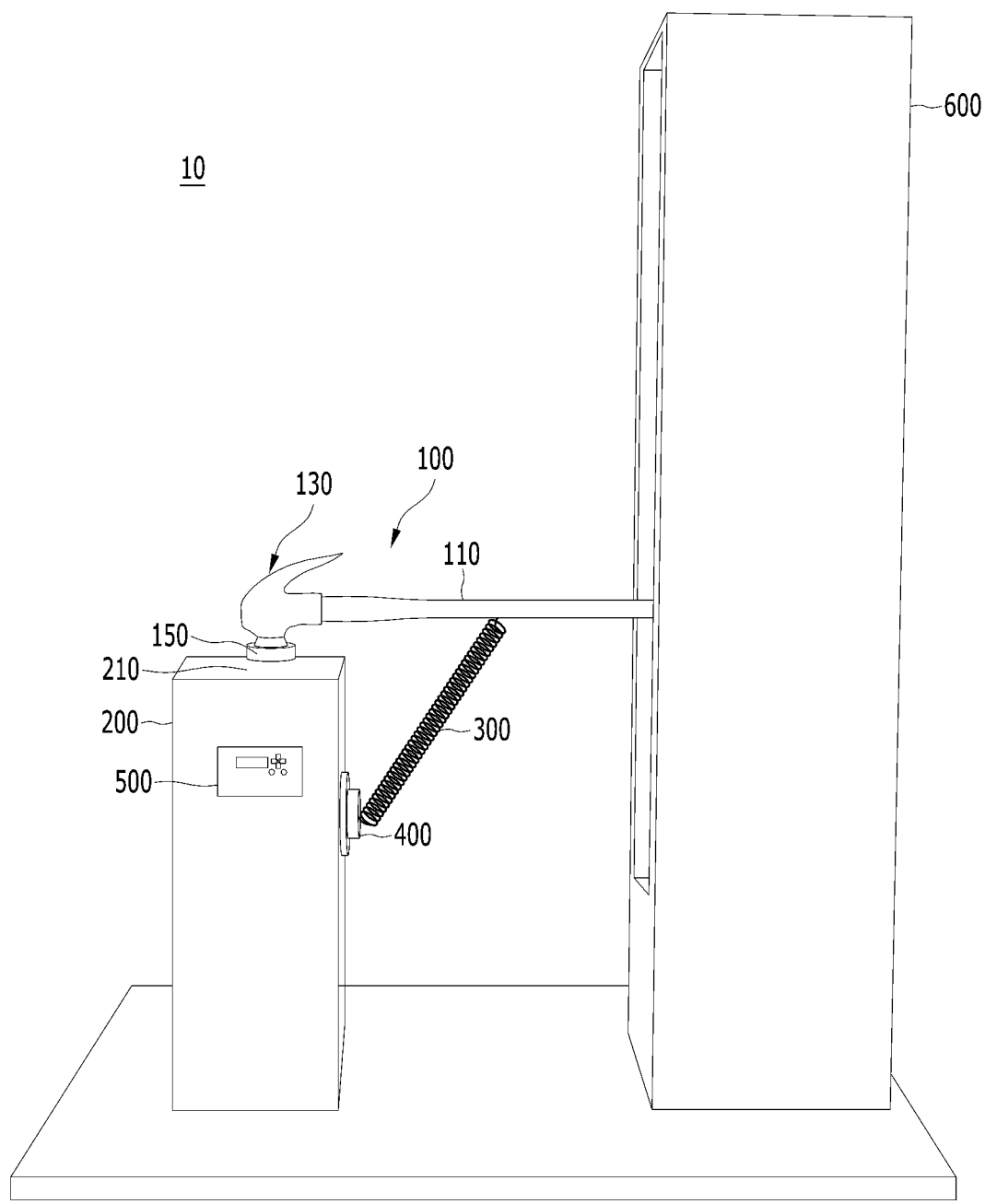
FIG. 1 is a side view of an impact blood splatters generation experiment apparatus capable of measuring an applied force according to an embodiment.

Hereinafter, embodiments will be described in detail with reference to the accompanying drawings. The same reference numerals are used to denote the same elements, and repeated descriptions thereof will be omitted.

It will be understood that although the terms "first," "second," etc. may be used herein to describe various components, these components should not be limited by these terms.

An expression used in the singular encompasses the expression of the plural, unless it has a clearly different meaning in the context.

It will be further understood that the terms "comprises" and/or "comprising" used herein specify the presence of stated features or components, but do not preclude the presence or addition of one or more other features or components.

It will be understood that when a layer, region, or component is referred to as being "formed on" another layer, region, or component, it can be directly or indirectly formed on the other layer, region, or component. That is, for example, intervening layers, regions, or components may be present.

Sizes of components in the drawings may be exaggerated for convenience of explanation. In other words, since sizes and thicknesses of components in the drawings are arbitrarily illustrated for convenience of explanation, the following embodiments are not limited thereto.

When a certain embodiment may be implemented differently, a specific process order may be performed differently from the described order. For example, two consecutively described processes may be performed substantially at the same time or performed in an order opposite to the described order.

It will be understood that when a layer, region, or component is connected to another portion, the layer, region, or component may be directly connected to the portion or an intervening layer, region, or component may exist, such that the layer, region, or component may be indirectly connected to the portion. For example, when a layer, region, or component is electrically connected to another portion, the layer, region, or component may be directly electrically connected to the portion or may be indirectly connected to the portion through another layer, region, or component.

Hereinafter, an impact blood splatters generation experimental apparatus 10 capable of measuring an applied force according to an embodiment will be described with reference to FIGS. 1 to 4.

Figure 2:
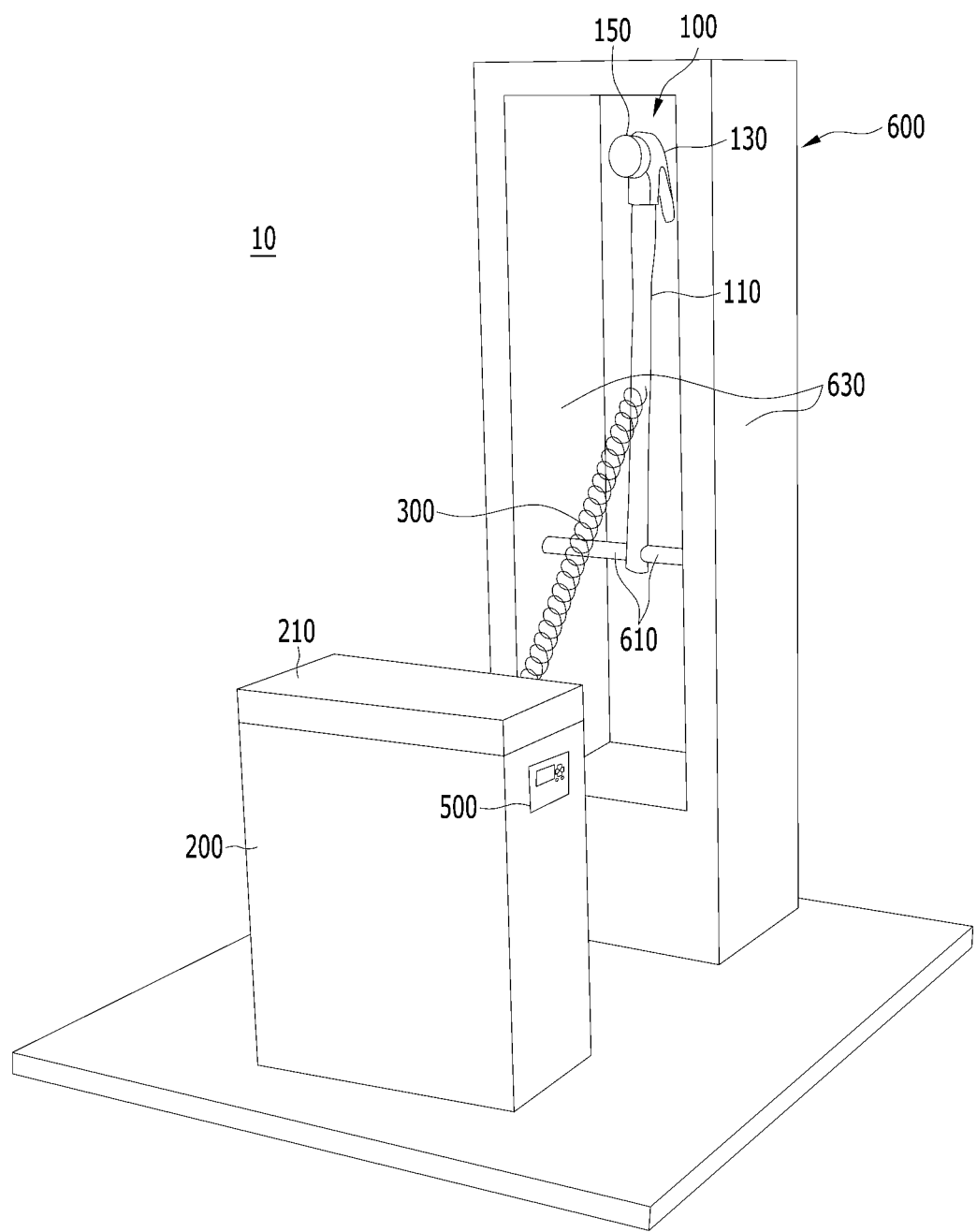
FIG. 2 is a perspective view illustrating a state in which a hammer is lifted in FIG. 1.
Figure 3:
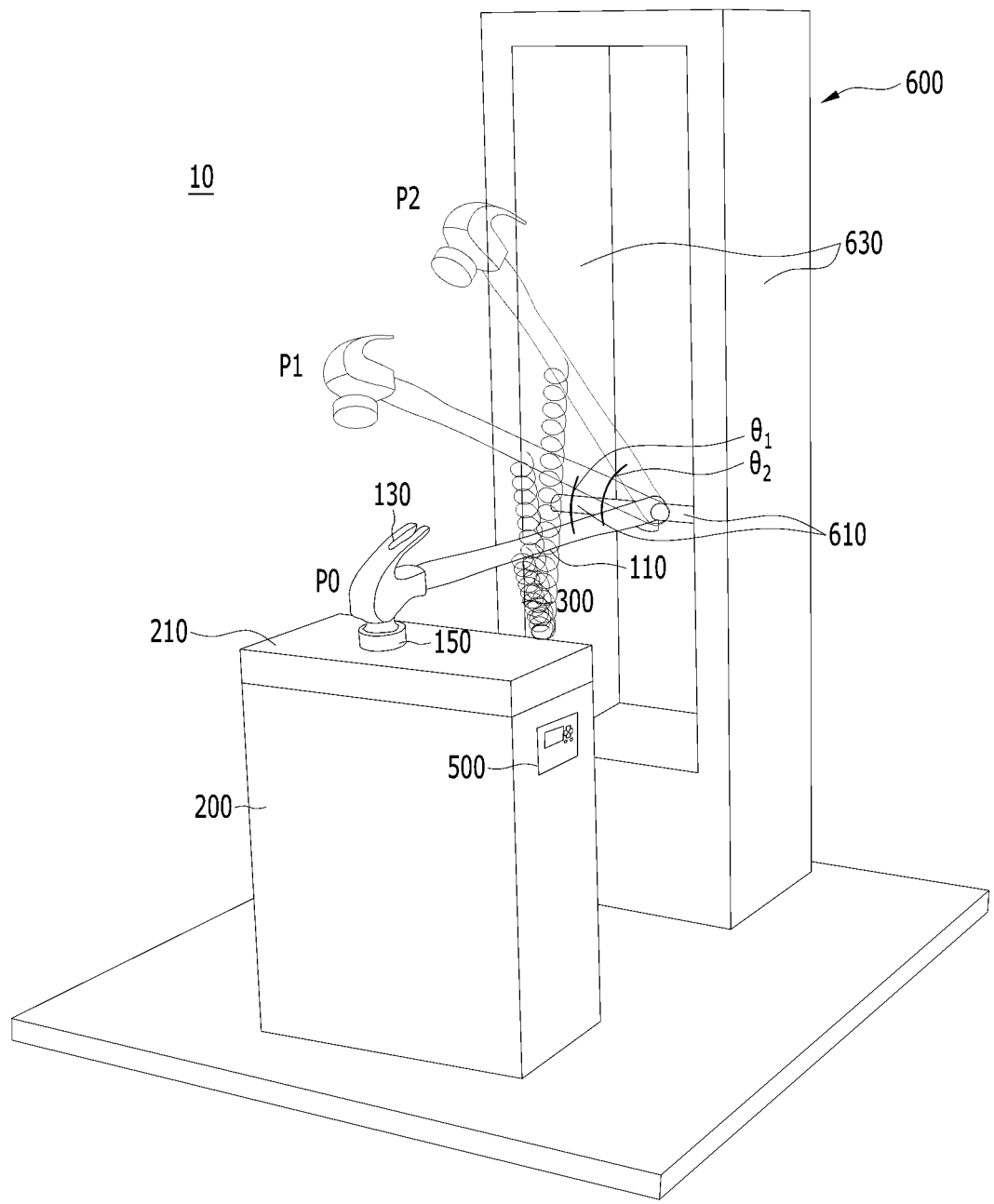
FIG. 3 is a view illustrating a state in which a hammer is rotating at a certain angle in FIG. 1.
Figure 4:
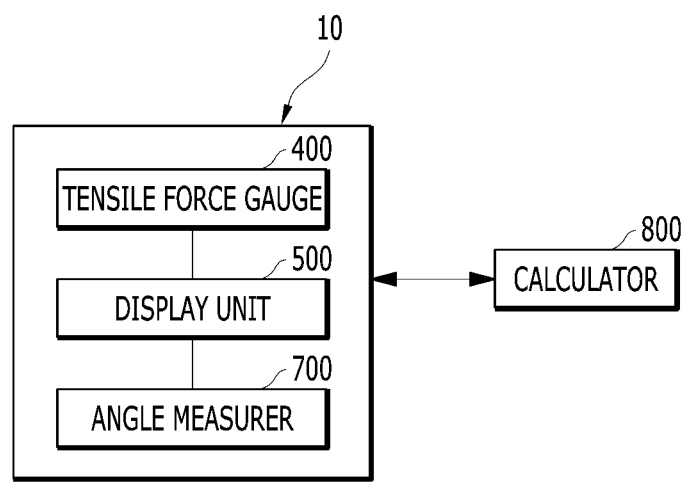
FIG. 4 is a block diagram of an impact blood splatters generation experimental apparatus capable of measuring an applied force according to an embodiment.

FIG. 1 is a side view of the impact blood splatters generation experimental apparatus 10 capable of measuring an applied force according to an embodiment, and FIG. 2 is a perspective view illustrating a state in which a hammer is lifted in FIG. 1. FIG. 3 is a view illustrating a state in which a hammer is rotating at a certain angle in FIG. 1, and FIG. 4 is a block diagram of an impact blood splatters generation experimental apparatus capable of measuring an applied force according to an embodiment.

Referring to FIGS. 1 to 4, the impact blood splatters generation experiment apparatus 10 capable of measuring the applied force according to an embodiment may include a hammer 100, a housing 200, an elastic member 300, a tensile force gauge 400, a display unit 500, and a support fixing member 600.

The hammer 100 may include a body portion 110, a head portion 130, and a striking portion 150. The body portion 110 is rod-shaped, and may be formed of wood or metal. The head portion 130 may be formed at one end of the body portion 110. The head portion 130 may be above the body portion 110 when a user lifts the hammer 100. The striking portion 150 may be formed on one side of the head portion 130. The striking portion 150 is a portion which may directly contact a striking surface 210 to be described later below when the hammer 100 is used and exert a strike. The striking portion 150 may be formed to be detachable from the head portion 130. The striking portion 150 may be formed in various types such that the area of the striking portion 150 which contacts the striking surface 210 may vary.

The housing 200 may include the striking surface 210 at an upper portion thereof such that the striking portion 150 may strike. The housing 200 has a constant height from the ground and may form an outer surface. The striking surface 210 is formed at a constant height from the ground and may receive a certain amount of blood. The striking portion 150 may strike the striking surface 210 in which a certain amount of blood is received. When the striking portion 150 strikes the striking surface 210, the blood may pop out to generate impact blood splatters on the wall or the ground. For example, the housing 200 may be formed in a tetrahedron or a cylindrical shape. As shown in the drawings, the housing 200 may be formed in a tetrahedron, but may be formed in various forms. The disclosure does not limit the shape of the housing 200.

The elastic member 300 is deformed by an external force, and has elasticity to return to its original shape when the force is removed. For example, the elastic member 300 may be a coil spring. One end of the elastic member 300 may be connected to the body portion 110, and the other end of the elastic member 300 may be connected to the tensile force gauge 400 to be described later below. One end of the elastic member 300 may be connected to any one point of the body portion 110. When a user lifts the hammer 100, the elastic member 300 connected to the body portion 110 is in an extended state. As such, when the user releases the hammer 100 in the state in which the elastic member 300 is extended, the striking portion 150 may strike the striking surface 210 by an elastic force of the elastic member 300.

The tensile force gauge 400 may be attached to the outer surface of the housing 200. The tensile force gauge 400 may be connected to the other end of the elastic member 300 having one end connected to the body portion 110. When the user lifts the hammer 100 to strike the striking surface 210, the elastic member 300 connected to one end of the body portion 110 of the hammer 100 is extended. Since the other end of the elastic member 300 is connected to the tensile force gauge 400, the tensile force gauge 400 may measure a force applied to the hammer 100 when the hammer 100 is lifted.

The display unit 500 may display the force applied to the hammer 100 measured by the tensile force gauge 400. The display unit 500 may be attached to the outer surface of the housing 200, so that the user may directly check the force applied to the hammer 100, thereby providing convenience to the user. The display unit 500 may display a value measured by the tensile force gauge 400 when the user lifts the hammer 100 to strike the striking surface 210.

The support fixing member 600 may include a support portion 610 and a fixing portion 630. The support fixing member 600 may support the hammer 100 when the striking portion 150 of the hammer 100 strikes the striking surface 210 and may fix the hammer 100 at a certain position on the ground.

The support portion 610 may be coupled to the other end of the body portion 110 in which the head portion 130 is formed at one end. While rotating the body portion 110 at a certain angle with the support portion 610 as an axis, the striking portion 150 may strike the striking surface 210. For example, the support 610 may be coupled to the body portion 110 to penetrate the other end of the body portion 110, so that the support portion 610 serves as a rotation axis when the body portion 110 rotates at a certain angle.

The fixing portion 630 is for fixing the support portion 610 to the ground. The fixing portion 630 fixes the support portion 610 to the ground, so that the hammer 100 may be fixed at a certain position. An end portion of the body portion 110 of the hammer 100 may be fixed at a certain position to provide convenience for the user to easily apply a constant force to the hammer 100.

The impact blood splatters generation experimental apparatus 10 capable of measuring the applied force according to an embodiment may further include an angle measurer 700.

The angle measurer 700 may measure a rotation angle of the body portion 110. When the user lifts the hammer 100, the body portion 110 may rotate at a certain angle with the support portion 610 as an axis. The angle measurer 700 may measure a rotation angle when the body portion 110 rotates with the support portion 610 as an axis.

Referring to FIG. 3, when the user lifts the hammer 100, the hammer 100 may move from the position of P0 to the positions of P1 and P2. When the user lifts the hammer 100 and moves it from P0 to the position of P1, the angle at which the body portion 110 of the hammer 100 rotates is $\theta_1$. In addition, when the user lifts the hammer 100 and moves it from P0 to the position of P2, the angle at which the body portion 110 of the hammer 100 rotates is $\theta_2$. As such, when the user lifts the hammer 100 and the body portion 110 moves while being changed to different rotation angles $\theta_1$ and $\theta_2$, the force applied to the hammer 100 may be changed according to the rotation angle of the body portion 110. According to the change in the angle at which the body portion 110 rotates, a measured value of the force applied to the hammer 100, the value being measured by the tensile force gauge 400, may change.

The impact blood splatters generation experimental apparatus 10 capable of measuring an applied force according to the disclosure may calculate the change in the force applied to the hammer 100 according to the change in an angle measured by the angle measurer 700 by a calculator 800 in a graph. The calculator 800 may be included in the impact blood splatters generation experimental apparatus 10 capable of measuring the applied force, but may be disposed outside and calculate a value provided from the impact blood splatters generation experimental apparatus 10 capable of measuring an applied force according to the disclosure.

The display unit 500 may display the angle measured by the angle measurer 700. The user may check the angle measured by the angle measurer 700 through the display unit 500, and at the same time, may check the force applied to the hammer 100. In addition, the user may check calculation results of the calculator 800 through the display unit 500. Therefore, the user may check a graph of a change in the force applied to the hammer 100 according to a change in the angle measured by the angle measurer 700 through the display unit 500.

Figure 5:
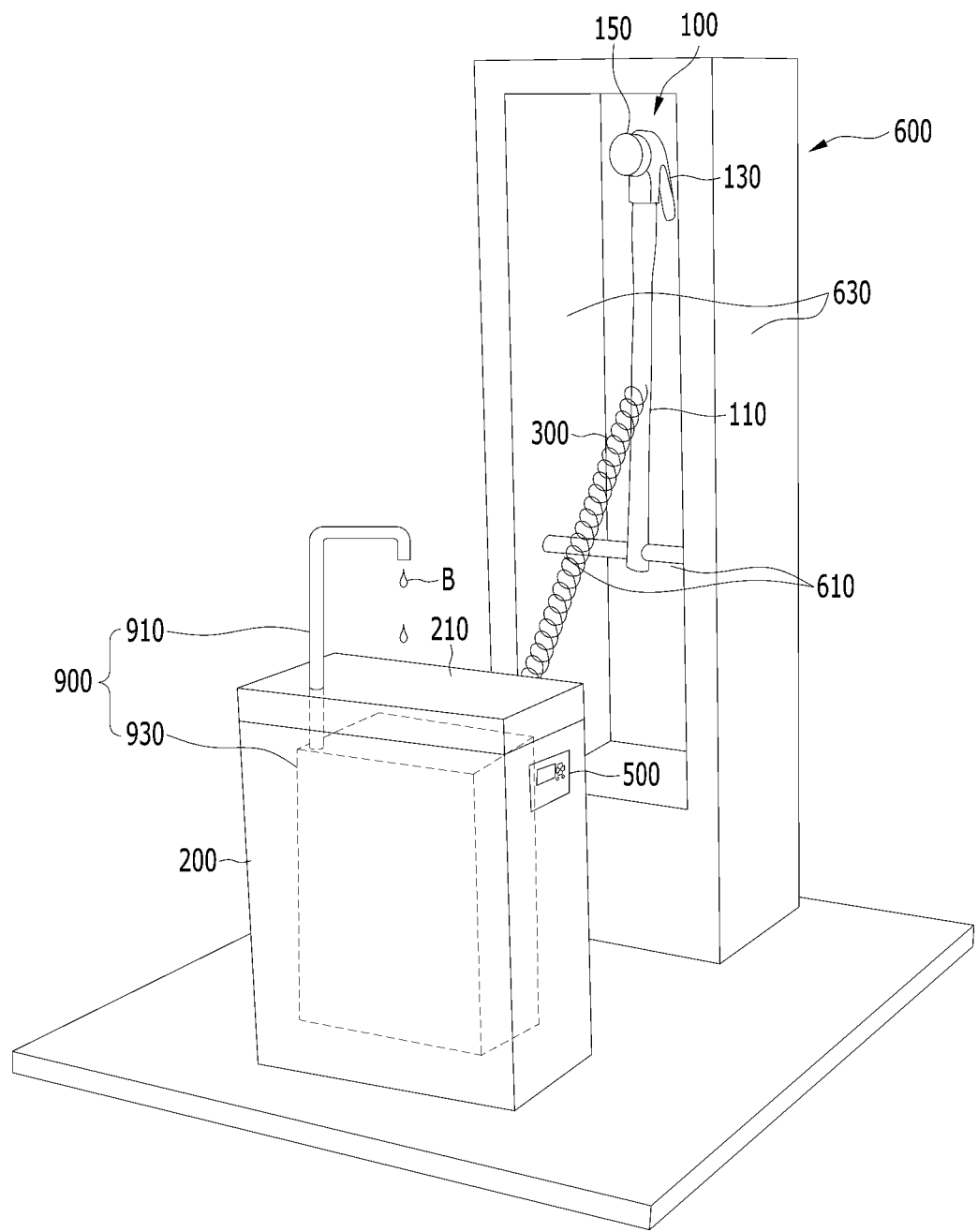
FIG. 5 is a schematic view of an impact blood splatters generation experimental apparatus capable of measuring an applied force according to another embodiment.

FIG. 5 is a schematic view of an impact blood splatters generation experimental apparatus capable of measuring an applied force according to another embodiment.

Referring to FIG. 5, the impact blood splatters generation experimental apparatus capable of measuring the applied force according to another embodiment may further include a blood injection member 900.

The blood injection member 900 may include a blood storage portion 910 and a blood injection portion 930.

The blood injection member 900 may store blood B at a certain temperature to inject a certain amount of blood B onto the striking surface 210.

The blood storage portion 910 may be located inside the housing 200 and may store the blood B to be discharged to the outside of the housing 200. The blood storage portion 910 may be maintained at about 37° C. such that the blood B may be stored at a temperature similar to the body temperature. The blood storage portion 910 may include a storage space for storing the blood B at a suitable temperature inside the housing 200 and a pump for discharging the blood B from the storage space. The blood storage portion 910 stores the blood B at a suitable temperature to discharge the blood B under similar environmental conditions as an actual bleeding case.

The blood injection portion 930 may inject a certain amount of blood B discharged from the blood storage portion 910 into a certain position of the striking surface 210. When generating impact blood splatters, it is possible to perform an experiment on a certain amount of blood B, thereby reconstructing bleeding cases more accurately.

Hereinafter, a method of generating impact blood splatters will be described using the impact blood splatters generation experimental apparatus 10 capable of measuring an applied force according to an embodiment with reference to FIG. 6.

Figure 6:
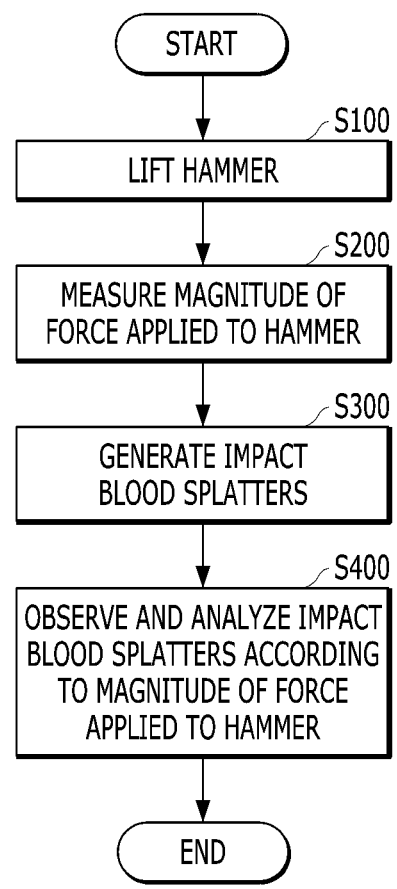
FIG. 6 is a flowchart illustrating a method of generating impact blood splatters using an impact blood splatters generation experimental apparatus according to an embodiment.

FIG. 6 is a flowchart illustrating a method of generating impact blood splatters using an impact blood splatters generation experimental apparatus according to an embodiment.

In operation S100, the hammer 100 including the rod-shaped body portion 110, the head portion 130 formed on one end of the body portion 110, the striking portion 150 formed on one side of the head portion 130 is lifted. The hammer 100 is lifted such that the striking portion 130 may strike the striking surface 210, so that the head portion 130 of the hammer 100 is located above the body portion 110 from the ground.

In operation S200, the tensile force gauge 400 connected to the other end of the elastic member 300 having one end connected to the body portion 110 measures the magnitude of force applied to the hammer 100. The tensile force gauge 400 is connected to the body portion 110 via the elastic member 300 to measure the force applied to the hammer 100. When the hammer 100 is lifted, since the body portion 110 is connected to one end of the elastic member 300, the elastic member 300 is extended by the force applied to the hammer 100.

In operation S300, the striking portion 150 strikes the striking surface 210 in which a certain amount of blood is received to generate impact blood splatters. The striking surface 210 may be formed on the upper portion of the housing 200 having a certain height from the ground. The tensile force gauge 400 may be attached to an outer surface of the housing 200. When the hammer 100 is lifted, the striking portion 150 may strike the striking surface 210 by an elastic force of the elastic member 300 in the extended state. In this case, impact blood splatters generated as the blood contained in the striking surface 210 splashes may be observed on the wall or the ground.

Thereafter, in operation S400, the shape and location of the impact blood splatters according to the magnitude of the force applied to the hammer 100 is observed and analyzed.

As described above, according to a method of generating impact blood splatters using the impact blood splatters generation experimental apparatus 10 capable of measuring an applied force according to an embodiment, the magnitude of force applied to the hammer 100, as well as the shape and location of impact blood splatters, may be analyzed and studied. Accordingly, the relationship between the impact blood splatters and the magnitude of the force applied to the hammer 100 may be analyzed and studied.

In addition, when the hammer 100 is lifted, the other end of the body portion 110 is rotatably fixed to rotate the body portion 110 at a certain angle, and a rotation angle of the body portion 110 may be changed. As such, operation S100 of lifting the hammer 100 by changing the rotation angle of the body portion 110, operation S200 of measuring the magnitude of the force applied to the hammer 100, operation S300 of generating impact blood splatters, and operation S400 of observing and analyzing the shape and location of the impact blood splatters may be performed. In this way, the shape and location of the impact blood splatters according to the rotation angle of the body portion 110 may be observed and analyzed.

The striking portion 150 may be formed to be detachable from the head portion 130. The striking portion 150 may be formed in various types such that the area of the striking portion 150 which contacts the striking surface 210 may vary, and may be detachable by being changed to another type. Here, operation S100 of lifting the hammer 150 while changing the type of the striking portion 150, operation S200 of measuring the magnitude of the force applied to the hammer 100, operation S300 of generating impact blood splatters, and operation S400 of observing and analyzing the shape and location of the impact blood splatters may be performed. In this way, the shape and location of the impact blood splatters according to the change in the area of the striking portion 150 which contacts the striking surface 210 may be observed and analyzed.

As described above, according to the impact blood splatters generation experimental apparatus 10 capable of measuring an applied force, and a method of generating impact blood splatters using the impact blood splatters generation experimental apparatus 10 according to embodiments, when impact blood splatters are generated, a force applied to the hammer 100 through the elastic member 300 may be displayed and confirmed by measuring with the tensile force gauge 400. Therefore, the user may be provided with convenience to observe and analyze the shape and location of the impact blood splatters together with the force applied to the hammer 100. In addition, the embodiments may accurately reconstruct a bleeding case, thereby contributing to proper resolution of criminal cases.

According to an embodiment, the shape and blood spot of impact blood splatters may be studied and analyzed together with an applied force, so that a bleeding case may be more accurately reconstructed. In addition, the impact blood splatters may be generated according to an embodiment to provide accurate analysis results for the evaluation and resolution of criminal cases.

The description herein is for the purpose of describing the inventive concept and numerous modifications and adaptations will be readily apparent to one of ordinary skill in the art without departing from the spirit and scope of the disclosure.

In this regard, the present embodiments may have different forms and should not be construed as being limited to the descriptions set forth herein. While the disclosure has been particularly shown and described with reference to embodiments thereof, it will be understood that various changes in form and details may be made therein without departing from the spirit and scope of the following claims.

What is claimed is:

1. An impact blood splatters generation experimental apparatus capable of measuring an applied force, the impact blood splatters generation experimental apparatus comprising:
   a hammer comprising a rod-shaped body portion, a head portion formed at one end of the body portion, and a striking portion formed on one side of the head portion;
   a housing receiving a certain amount of blood thereon and comprising a striking surface on which the striking portion may strike;
   a tensile force gauge attached to an outer surface of the housing;
   an elastic member having one end connected to the body portion and the other end connected to the tensile force gauge; and
   a display unit displaying a force applied to the hammer, the force being measured by the tensile force gauge, when a user lifts the hammer to strike the striking surface.

2. The impact blood splatters generation experimental apparatus of claim 1, further comprising:
   a support fixing member comprising a support portion coupled to the other end of the body portion such that the striking portion strikes the striking surface while the body portion rotates at a constant angle; and a fixing portion fixing the support portion to the ground.

3. The impact blood splatters generation experimental apparatus of claim 1, further comprising:
   a blood injection member comprising a blood storage portion located inside the housing and storing and discharging the blood; and a blood injection portion injecting a certain amount of blood discharged from the blood storage portion into a certain position of the striking surface.

4. The impact blood splatters generation experimental apparatus of claim 2, further comprising:
   an angle measurer measuring a rotation angle of the body portion, wherein the display unit further displays an angle measured by the angle measurer.

5. A method of generating impact blood splatters using an impact blood splatters generation experimental apparatus capable of measuring an applied force, the method comprising:
   lifting a hammer comprising a rod-shaped body portion, a head portion formed at one end of the body portion, and a striking portion formed on one side of the head portion;
   measuring the magnitude of force applied to the hammer by a tensile force gauge connected to the other end of the elastic member having one end connected to the body portion;
   generating impact blood splatters by striking a striking surface in which a certain amount of blood is received by the striking portion; and observing and analyzing the shape and location of the impact blood splatters according to the magnitude of the force applied to the hammer.

6. The method of claim 5, wherein the striking surface has a constant height from the ground and is formed on an upper surface of a housing with the tensile force gauge on the outer surface.

7. The method of claim 5, wherein the lifting of the hammer, the measuring of the magnitude of the force applied to the hammer, the generating of impact blood splatters, and the observing and analyzing of the shape and location of the impact blood splatters are performed by rotatably fixing the other end of the body portion so as to rotate the body portion at a certain angle when the hammer is lifted, and by changing a rotation angle of the body portion.

* * * * *